(12) United States Patent
Van Driel et al.

US010724078B2

(10) Patent No.: US 10,724,078 B2
(45) Date of Patent: Jul. 28, 2020

(54) SPATIAL MAPPING OF MOLECULAR PROFILES OF BIOLOGICAL TISSUE SAMPLES

(71) Applicant: KONINKLIJKE PHILIPS N.V., Eindhoven (NL)

(72) Inventors: Marc Van Driel, Eindhoven (NL); Reinhold Wimberger-Friedl, Eindhoven (NL); Anke Pierik, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/565,851

(22) PCT Filed: Apr. 13, 2016

(86) PCT No.: PCT/EP2016/058067
§ 371 (c)(1),
(2) Date: Oct. 11, 2017

(87) PCT Pub. No.: WO2016/166128
PCT Pub. Date: Oct. 20, 2016

(65) Prior Publication Data
US 2018/0112261 A1    Apr. 26, 2018

(30) Foreign Application Priority Data

Apr. 14, 2015  (EP) .................................... 15163481

(51) Int. Cl.
*C12Q 1/6841*      (2018.01)
*C12Q 1/6869*      (2018.01)
*C12Q 1/6844*      (2018.01)
*C12Q 1/6837*      (2018.01)

(52) U.S. Cl.
CPC ......... *C12Q 1/6841* (2013.01); *C12Q 1/6844* (2013.01); *C12Q 1/6869* (2013.01); *C12Q 1/6837* (2013.01); *C12Q 2535/00* (2013.01); *C12Q 2543/101* (2013.01)

(58) Field of Classification Search
CPC .............................. C12Q 1/6841; C07H 21/04
See application file for complete search history.

(56) References Cited

U.S. PATENT DOCUMENTS

2005/0123181 A1     6/2005  Freund
2011/0245111 A1*   10/2011  Chee ................... C12Q 1/6837
                                                                  506/35
2012/0045790 A1*    2/2012  Van Dijk .............. G06T 7/0014
                                                                  435/29
2014/0066318 A1     3/2014  Frisen

FOREIGN PATENT DOCUMENTS

WO          2012140224 A1    10/2012
WO          2014053955 A1     4/2014
WO     WO 2014/210223    * 12/2014
WO     WO 2014/210225    * 12/2014

OTHER PUBLICATIONS

Crosetto et al , Spatially resolved transcriptomics and beyond, 2015, Nature Reviews/ Genetics, 6, 57-66. (Year: 2015).*
Rongqin Ke et al, In situ sequencing for RNA analysis in preserved tissue and cells, 2013, Nature Methods, 9, 857-860 (Year: 2013).*
Rongqin Ke et al, Supplemental information, In situ sequencing for RNA analysis in preserved tissue and cells, 2013, Nature Methods, 9, 857-860, pp. 1-6 (Year: 2013).*
Almendro, Vanessa et al "Inference of Tumor Evolution during Chemotherapy by Computational Modeling and In Situ Analysis of Genetic and Phenotypic Cellular Diversity", Cell Reports, vol. 6, 2014, pp. 514-527.
Ke, Rongqin et al "In Situ Sequencing for RNA Analysis in Preserved Tissue and Cells", Nature Methods, vol. 10, No. 9, 2013.
Danaher, Patrick et al "Facile semi-automated forensic body fluid identification by multiplex solution hybri dization of NanoString—barcode probes to specific mRNA targets". Forensic Science International: Genetics, vol. 14, 2015, pp. 18-30.
Armani et al., "2D-PCR: A Method of Mapping DNA in Tissue Sections", Lab Chip 9:24, Dec. 2009, pp. 3526-3534.
Armani et al., "Quantifying mRNA Levels Across Tissue Sections witages 2D-RT-Qpcr", Anal Bioanal Chem, 400, (2011), pp. 3383-3393.
Sambrook J. et al., "Molecular, Cloning, A Laboratory Manual", 2nd ed., Edited by J. Sambrook, E.F. Fritsch, and T. Maniatis. Cold Spring Harbor Laboratory Press, Cold Spring Harbor, NY, 1989.
Andersson et al., "Analysis of Protein Expression in Cell Microarrays: A Tool for Antibody-based Proteomics", Journal of Histochemistry & Cytochemistry, vol. 54, No. 12, pp. 1413-1423, 2006.
Gill P. et al., "Nucleic Acid Isothermal Amplification Technologies—A Review", 2008, Nudeosides Nucleotides Nucleic Acids, vol. 27, No. 3, pp. 224-243.

(Continued)

*Primary Examiner* — Narayan K Bhat
(74) *Attorney, Agent, or Firm* — Sherry Austin

(57) ABSTRACT

A method is presented that enables the spatial mapping of nucleic acids of tissue samples with high resolution and without sacrificing the degree of multiplexing that is available from next-generation sequencing. The method is based on the application of patterns of barcoded oligonucleotides probes onto predefined locations in a region of interest in a tissue sample. Every nucleic acid analyzed can be allocated to a certain position inside the sample based on the barcode. Various printing technologies can be used and different ways of patterning can be employed, like a regular array with a certain pitch or alternatively an object-based patterning with defined regions of interest without shape constraints.

28 Claims, 3 Drawing Sheets

Specification includes a Sequence Listing.

(56) References Cited

OTHER PUBLICATIONS

Tullis et al., "Calcium Protects DNase I from Proteinase K: A New Method for the Removal of Contaminating RNase from DNase I", Analytical Biochemistry, 1980, vol. 107, No. 1, pp. 260-264.

* cited by examiner

SPATIAL MAPPING OF MOLECULAR PROFILES OF BIOLOGICAL TISSUE SAMPLES

CROSS-REFERENCE TO PRIOR APPLICATIONS

This application is the U.S. National Phase application under 35 U.S.C. § 371 of International Application No. PCT/EP2016/058067, filed on Apr. 13, 2016, which claims the benefit of European Patent Application No. 15163481.3, filed on Apr. 14, 2015. These applications are hereby incorporated by reference herein.

FIELD OF THE INVENTION

A method is presented that enables the spatial mapping of nucleic acids of tissue samples with high resolution. The method is based on the application of patterns of oligonucleotide probes comprising a barcode sequence that bind to the nucleic acids in the sample taking into account tissue information.

BACKGROUND OF THE INVENTION

Currently, pathologists are performing microscopic examinations of various forms of tissue and cells. The microscopic image reveals information on morphology (e.g. cell types, differentiation, etc.), which is the basis for the diagnosis. In case the pathologist wants to examine the tissue/cells in more detail, biomarker-specific staining protocols are used, such as ER, PR, and HER2 in the case of breast cancer. Certain molecular tests are carried out in situ by so-called in-situ hybridization on DNA and RNA. The number of targets however is limited in such an approach. For improved stratification, molecular diagnostic tests are carried out to test gene expression (e.g. OncoTypeDX, Mammaprint) or to look for actionable mutations, like KRAS, EGFR, etc. with the aid of sequencing (e.g. Sanger or next generation sequencing) and expression profiling (e.g. micro-arrays, RNAseq, RT-PCR).

Tumor tissue is heterogeneous in composition and surrounded by stromal and infiltrating immune cells. This spatial heterogeneity can affect the molecular analysis, as the DNA and RNA of the tumor cells is diluted by DNA and RNA from cells that are not targeted by the analysis. To overcome this problem regions of interest (ROI) of the tissue/cells are selected on the slide and removed from the slide, for example, by scraping or (laser capture) micro dissection techniques, to be processed and analyzed in molecular assays and/or proteomic assays (protein compositions etc.). While collecting ROIs only limited positional information is stored and often the collected material is originating from different ROIs or ROIs are pooled and subsequently analyzed together. In case of laser capture micro dissection, small regions can be collected separately, but this is time consuming and does not allow for systematic analysis of the tissue/cells. Molecular analyses are time consuming and expensive. For a higher resolution mapping of molecular profiles this results in a large number of molecular tests with costs that would be too high for clinical practice. Tumor heterogeneity and tissue architecture may furthermore be a potential diagnostic parameter as they can provide clues about the clonal evolution of the tumor and its aggressiveness. Thus by removing ROIs from the slide in order to perform further molecular analyses this information is lost.

Heterogeneity maps have been created based on in-situ staining for molecular and protein biomarkers. See for example Almendro, et al., 2014, Cell Reports, 6: 514-527. A different approach was described by Armani et al., Lab Chip, 2009, 9(24): 3526-3534 and Armani et al., Anal Bioanal Chem, 2011, 400: 3383-3393, where a tissue slice was pressed into a well plate where in each well a single qPCR or RT-qPCR reaction was performed. Subsequently, a 2D map was generated of the amplified target.

US20140066318 A1 describes a probe array on a substrate onto which a tissue sample is placed. The probes bind to target nucleic acids and bound probe and target nucleic acid are extracted and used for molecular diagnosis.

In the present application we describe an approach that allows a high spatial resolution mapping of nucleic acids without sacrificing the degree of multiplexing that is available from next-generation sequencing by efficiently using multiplexing ROIs per sample. The method of the invention is based on the application of patterns of oligonucleotide probes comprising a barcode sequence taking into account tissue information, wherein the oligonucleotide probes bind to the nucleic acids in the sample. Various application technologies can be used and different ways of patterning can be employed, like a regular array with a certain pitch or alternatively an object-based patterning with defined regions of interest without shape constraints.

A key aspect of the invention is the identification of a ROI and defining the spatial resolution of the pattern individually based on the tissue information and question to be answered. The region of interest as well as the spatial resolution of the pattern can be chosen in response to image-based analysis of the tissue before the application of the reagents. By identification of at least one ROI and only providing oligonucleotide probes to the ROI, fewer species of oligonucleotide probes are required to provide a spatial map. Further, designing spatial resolution patterns individually without being restricted to an array format allows the number of oligonucleotide probes to be used to be determined on an individual basis. The method of the invention is therefore much cheaper than common prior art methods and compatible with selective profiling.

Another advantage of the method of the invention is that it fits smoothly in the current digital pathology workflow. The common digital pathology workflow is:
1. preparation of a hematoxylin and eosin stain staining slide,
2. scanning the hematoxylin and eosin stain slide to obtain a digital image
3. perform an image analysis to arrive at a pathological diagnosis (benign or malignant), and
4. concurrently identify ROIs for further molecular diagnosis to provide more precise diagnosis results.

SUMMARY OF THE INVENTION

The invention relates to a method for spatial detecting nucleic acids in a tissue sample comprising the steps of:
identifying at least one region of interest (ROI) within the sample;
applying at least one species of oligonucleotide probes onto predefined locations within the ROI and allowing the oligonucleotide probes to bind to the nucleic acids of the sample, wherein the oligonucleotide probes comprise a barcode sequence;
extracting the nucleic acid-oligonucleotide probes complexes;
sequencing the extracted nucleic acid molecules;

correlating the sequenced nucleic acid molecules to the initial location of the corresponding targeted nucleic acid molecules within the ROI to generate a spatial distribution of the targeted nucleic acid molecules, wherein each location is identified by one or more species of oligonucleotide probes bound in step b).

In one embodiment, DNA molecules are generated from the nucleic acid-oligonucleotide probes complexes via DNA amplification prior to step d).

In another embodiment, the generation of DNA molecules occurs after a reverse transcription reaction.

In one embodiment, the binding of the oligonucleotide probes to the nucleic acids of the sample in step b) occurs via hybridization, wherein the oligonucleotide probes are used as primers.

In an alternative embodiment, the binding of the oligonucleotide probes to the nucleic acids of the sample in step b) occurs via ligation.

In one embodiment, step e) further comprises correlating the spatial distribution of the targeted nucleic acid molecules with an image of the ROI or with an image of the tissue sample in which the ROI was identified obtained before or after step b).

In one embodiment, the method further comprises providing a two-dimensional spatial map to visualize the spatial distribution of the targeted nucleic acid molecules.

In one embodiment, the method further comprises overlaying the two-dimensional spatial map with the image of the ROI or with the image of the tissue sample in which the ROI was identified obtained before or after step b).

In one embodiment, at least two different species of oligonucleotide probes are bound to one targeted nucleic acid molecule in step b), wherein the unique combination of the at least two different species of oligonucleotide probes is used to identify the location of the targeted nucleic acid molecules within the ROI.

In one embodiment, at least one of the species of oligonucleotide probes that bind to one nucleic acid molecule comprises a generic sequence, wherein optionally the generic sequence is complementary to the targeted nucleic acid.

In one embodiment, at least one of the species of oligonucleotide probes that bind to one nucleic acid molecule comprises an additional sequence, wherein the additional sequence is a purification sequence or a primer alignment sequence.

In one embodiment, the predefined locations are defined by a separation mask.

In one embodiment, the separation mask is a top separation mask, optionally printed onto the sample, or a full separation mask, wherein the separation mask is a lattice separation mask, a freeform separation mask or a combination thereof.

In one embodiment, the oligonucleotide probes are applied in step b) onto the predefined locations by liquid transfer technologies, preferably by contact printing techniques or non-contact printing techniques, such that the applied oligonucleotide probes do not intermix between different predefined locations.

In one embodiment, the sample is a histopathological specimen, preferably a deparaffinised formalin-fixed paraffin-embedded (FFPE) sample, a fresh frozen (FF) sample or a fresh sample, or a cytology sample.

In one embodiment, the targeted nucleic acid molecule is RNA.

In one embodiment, the targeted nucleic acid molecule is DNA.

Figure 1:
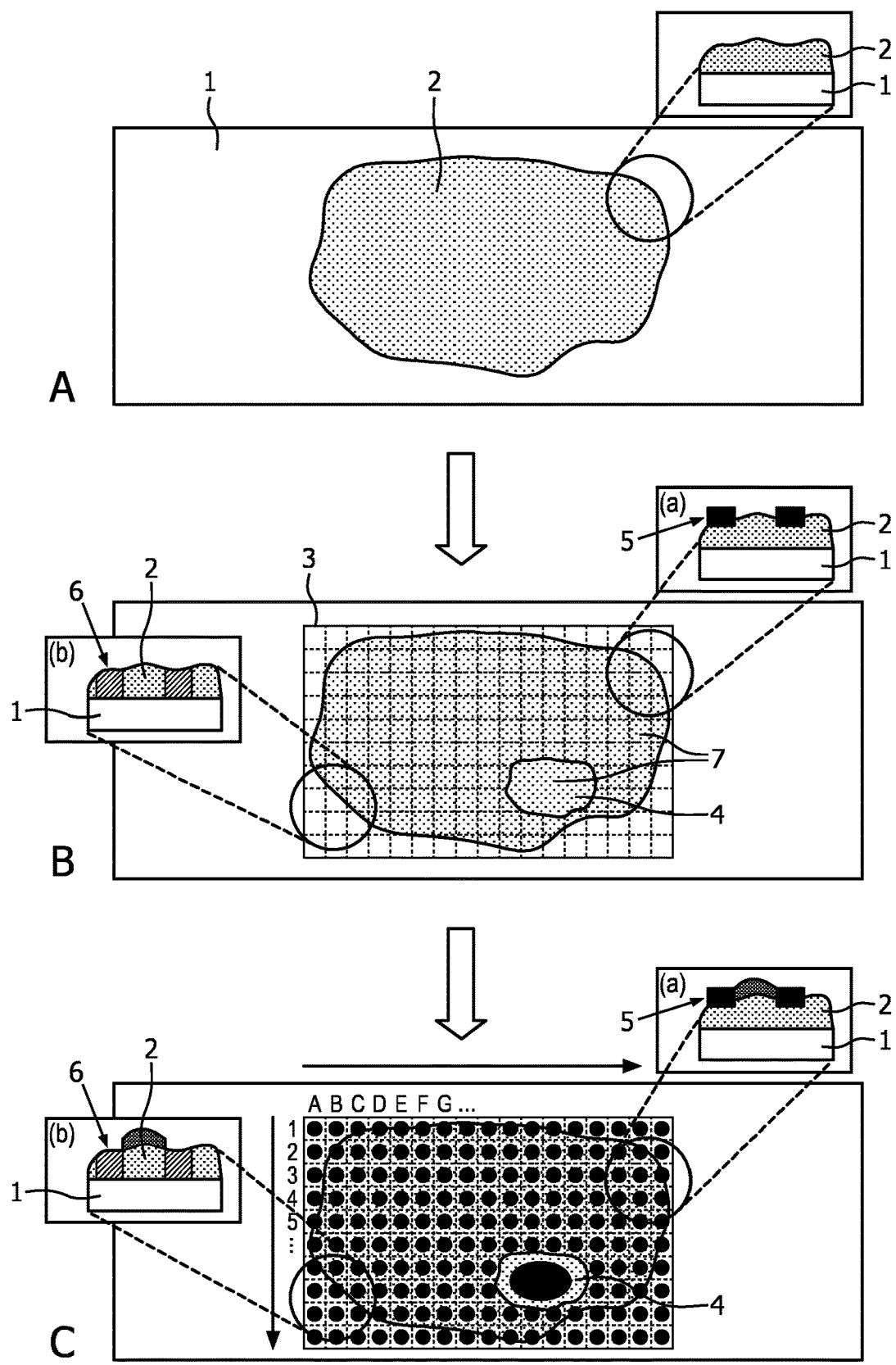
FIG. 1 Overview of the invention. (A) Supporting material 1 and tissue sample 2 are shown in a top view and in a small panel in the side view. (B) A separation mask has been applied on top of the tissue sample creating predefined locations 7. The depicted separation mask combines a lattice separation mask 3 and a freeform separation mask 4. However, the lattice separation mask and the freeform separation mask 4 can be also applied individually. Two types of separation masks with different cross-section structures are shown in the panels providing the side view: (a) top separation mask 5, (b) full separation mask 6. (C) Oligonucleotide probes have been applied in a liquid phase onto the predefined locations of the tissue sample. The panels provide the side view: (a) top separation mask 5, (b) full separation mask 6.

FIGS. Amplification curves A, B and C are shown.

DETAILED DESCRIPTION OF EMBODIMENTS

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The present invention relates to the spatial mapping of nucleic acids in a sample.

The term "spatial mapping", as used herein, relates to the assignment of targeted nucleic acids to their spatial location in the sample. A spatial map may provide transcriptional or genomic information from multiple cells in a tissue sample wherein the information is characterized by a two-dimensional spatial resolution. A spatial map may be created based on an array or may have a unique spatial resolution since patterns may be chosen based on individual features of the ROI as well as in response to image-based analysis of the tissue before the application of the reagents. The spatial distribution of the targeted nucleic acids may be correlated with an image of the ROI or with an image of the tissue sample in which the ROI was identified to provide a visualization of the spatial map. Thus, the method according to the invention provides an individualized spatial map which may be designed based on the question to be answered taking into account tissue information.

The term "nucleic acid", as used herein, denotes any nucleic acid molecule that can be detected by using the methods herein. Nucleic acid molecules include naturally occurring nucleic acids such as deoxyribonucleic acid (DNA) or ribonucleic acid (RNA) as well as artificially designed nucleic acids, e.g. nucleic acid analogs chemically synthesized or generated by means of recombinant gene technology (see, for example, Sambrook, J. et al. (1989) *Molecular, Cloning: A Laboratory Manual,* 2nd ed., Cold Spring Harbor Laboratory Press, Cold Spring Harbor, N.Y.). Specific examples of artificially designed nucleic acids include peptide nucleic acids (PNA) or locked nucleic acids (LNA). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. The nucleic acids can be of any length and can be either single-stranded or double-stranded molecules. As used herein, the term "nucleotide" is to be understood as referring to both ribonucleotides and deoxyribonucleotides (i.e. RNA and DNA molecules). In one embodiment the nucleic acid is DNA. In another embodiment the nucleic acid is RNA.

The term "targeted nucleic acid" or "target nucleic acid", as used herein, denotes the nucleic acid or nucleic acids to be mapped. In one embodiment, the target nucleic acid relates to all nucleic acids in the sample, preferably to all DNA or to all RNA of the sample. In another embodiment the target nucleic acid relates to all nucleic acids of a specific type in the sample, for example, mRNA, tRNA or rRNA. In another embodiment, the target nucleic acid is one or more specific nucleic acid of interest. The nucleic acid of interest may be any gene of a genome, preferably any gene of the human genome. For example, the target nucleic acid may be associated with a disease, for example, a malignant disease such as cancer, inflammation, bacterial infection or viral infection. Examples of such nucleic acids include nucleic acids specific for or produced by a pathogen or the diseased cells or tissue, as well as nucleic acids produced in response to a disease such as nucleic acids encoding cytokines or antigens. Targeted nucleic acids may have any size. In one embodiment the targeted nucleic acid is DNA. In another embodiment the targeted nucleic acid is RNA. In a preferred embodiment the targeted nucleic acid is RNA, preferably all mRNA of the sample.

The target nucleic acid may be fragmented or intact. In one embodiment the target nucleic acid is fragmented. Fragmented nucleic acids may be produced by any means known in the art such as physical methods, for example, sonication or ultrasound treatment, chemical methods or enzymatic methods, for example, with endonucleases such as restriction enzymes. Fragmentation may be done before, during or after identifying the ROI in the tissue sample. In one embodiment, fragmentation is achieved in the step of fixing tissue. For example, the freezing of the sample or fixation of the sample with formalin may result in at least partial fragmentation of the nucleic acids. Other fixatives may produce similar results. A fragmented nucleic acid may be up to about 20000 nucleotides in length. Typically, fragmented nucleic acids are 10 to 10000 nucleotides in length, e.g. 20 to 2000 nucleotides, 30 to 1000 nucleotides or 50 to 500 nucleotides. Fragmentation of nucleic acids may not result in all nucleic acids being fragmented. Thus, after fragmentation the nucleic acids may be partially fragmented. In a preferred embodiment, the nucleic acids are at least partially fragmented. In another embodiment, the nucleic acids are intact. In one embodiment the targeted nucleic acid is fragmented DNA or fragmented RNA. In another embodiment the targeted nucleic acid is intact DNA or intact RNA. In a preferred embodiment, the targeted nucleic acid is at least partially fragmented RNA, preferably all mRNA of the sample.

The term "nucleic acid molecule", as used herein, refers to one specific nucleic acid molecule that is present in the predefined location within the ROI. For example, in embodiments where all mRNA within the ROI is to be targeted, a nucleic acid molecule represents one mRNA molecule.

The term "sample", as used herein, denotes any biological sample that can be derived from any organism, for example, plant, animal, fungi, human or any artificial sample. In a preferred embodiment, the sample is a tissue sample. The "tissue sample" may be a harvested, cultured or biopsied tissue sample or a part thereof. The tissue sample may be derived from diseased tissue such as cancer tissue, inflamed tissue or infected tissue, tissue adjacent to diseased tissue, or healthy tissue. In a preferred embodiment the tissue sample is derived from diseased tissue or tissue adjacent thereto.

The tissue sample may be a biological tissue sample or an artificial tissue sample. A "biological tissue sample" refers to a naturally occurring ensemble of cells and includes clinical samples derived from biopsy or surgery, cytology samples or cultured cells forming a tissue. The biological tissue sample can be prepared by any conventional method of tissue sample preparation. In one embodiment the biological tissue sample is a histopathological specimen. In another embodiment the biological tissue sample is a cytology sample. An "artificial tissue sample" is prepared from cells not naturally forming a solid tissue, e.g. blood or suspension cell cultures. An artificial tissue sample may be prepared from a cell suspension obtained from clinical samples, such as whole blood, lymph or CSF, or from cell suspensions obtained by in vitro methods. The cells may be captured in a matrix such as a gel matrix and sectioned by conventional methods as described, for example, by Andersson et al., 2006, J Histochem Cytochem 54(12): 1413-23. The artificial tissue sample may be a single cell layer or comprise multiple cell layers. In one embodiment the artificial tissue sample is prepared from a cell suspension obtained from clinical samples. In another embodiment the artificial tissue sample is prepared from a cell suspension obtained by in vitro methods. In a preferred embodiment the tissue sample is a biological tissue sample, preferably a clinical sample, even more preferably a histopathological specimen or cytology sample.

The tissue sample may have a layer of cells with a thickness of approximately 1 cell or less. In one embodiment the thickness of the tissue sample will be less than 0.9, 0.8, 0.7, 0.6, 0.5, 0.4, 0.3, 0.2 or 0.1 of the cross-section of a cell. In another embodiment the tissue sample may have a thickness of greater than 1 cell. In one embodiment the thickness of the tissue sample section will be at least about 0.1 Gm, preferably at least about 0.2, 0.3, 0.4, 0.5, 0.7, 1.0, 1.5, 2, 3, 4, 5, 6, 7, 8, 9 or 10 µm. In other embodiments the thickness of the tissue sample section is at least about 10, 11, 12, 13, 14, 15, 20, 30, 40 or 50 µm. Thicker samples may also be used if desired or convenient, for example, the tissue sample may have a thickness of about 70 or 100 µm or more. Typically, the thickness of the tissue sample section is between about 1-100 µm, 1-50 µm, 1-30 µm, 1-25 µm, 1-20 µm, 1-15 µm, 1-10 µm, 3-10 µm, 2-8 µm, 3-7 µm or 4-6 µm. In a preferred embodiment the tissue sample has a thickness in the range of 3-10 µm. The thickness of the tissue sample is not critical for the method of the invention and the values are representative values only.

The tissue sample may have a size of about 2 cm². In one embodiment the tissue sample has a length of about 0.5, 0.6, 0.7, 0.8, 0.9, 1.0, 1.2, 1.5, 1.7, 2.0, 2.5, 3.0, 3.5, or 4.0 cm or any number in between and a height of about 0.2, 0.3, 0.4, 0.5, 0.6, 0.7, 0.8, 0.9, 1.0, 1.2, 1.5, 1.7 or 2.0 cm or any number in between. The height and length of the sample are interchangeable. In a specific embodiment the tissue sample has a maximum size of 2.0 by 4.0 cm. In another embodiment the tissue sample has an area of about 0.5, 0.6, 0.7, 0.8, 0.9, 1.0, 1.2, 1.5, 1.7, 2.0, 2.5, 3.0, 3.5, 4.0, 4.5, 5.0, 5.5, 6.0, 6.5, 7.0, 7.5 or 8.0 cm² or any number in between. In a preferred embodiment the tissue sample has a maximum size of about 2.0 by 4.0 cm, preferably the tissue sample has an area in the range of about 1.0 to 5.0 cm², more preferably the area is about 2.0 cm².

The tissue sample may be fresh, frozen, fixed or unfixed. In one embodiment the tissue sample is a fresh sample. In another embodiment the tissue sample is a fresh frozen sample. In yet another embodiment the tissue sample is a fixed tissue sample. Any procedure known in the art may be used for freezing, fixing or embedding the tissue sample. In particular, any known fixatives or embedding materials may be used. In a one embodiment the tissue sample is a deparaffinised formalin-fixation and paraffin-embedded (FFPE) sample. In a preferred embodiment the tissue sample is a FFPE sample, fresh frozen sample or fresh sample of a histopathological specimen or cytology sample, preferably a FFPE sample of a histopathological specimen.

In one aspect, the invention relates to a method for spatial detecting nucleic acids in a tissue sample comprising the steps of:

identifying at least one region of interest (ROI) within the sample;

applying at least one species of oligonucleotide probes onto predefined locations within the ROI and allowing the oligonucleotide probes to bind to the nucleic acids of the sample, wherein the oligonucleotide probes comprise a barcode sequence;

extracting the nucleic acid-oligonucleotide probes complexes;

sequencing the extracted nucleic acid molecules;

correlating the sequenced nucleic acid molecules to the initial location of the corresponding targeted nucleic acid molecules within the ROI to generate a spatial distribution of the targeted nucleic acid molecules, wherein each location is identified by one or more species of oligonucleotide probes bound in step b).

The term "method for spatial detecting", as used herein, relates to a method for detecting target nucleic acids and identifying the initial location of said nucleic acids in the sample.

The "targeted nucleic acid molecules" correspond to the nucleic acids of the sample that were bound by the oligonucleotide probes in step b).

The region of interest (ROI) may be identified in the tissue sample taking into account tissue information which may be obtained according to any procedure known in the art. For example, the tissue sample may be imaged, stained or labeled by suitable markers. In one embodiment the ROI is identified by staining. In another embodiment the ROI is identified by labeling with suitable markers. In yet another embodiment the ROI is identified by imaging. In a preferred embodiment the ROI is identified based on image analysis. Image analysis may be done automatically or manually. In case of automatic ROI selection image analysis is needed. All common methods of performing image analysis may be used.

The ROI, as referred herein, may also comprise the surrounding area of the identified ROI, i.e. the area directly adjacent to the region identified as being of interest. The ROI may have any size between the same size as the tissue sample (maximum size) and the lattice cell size (minimum size). It is preferred that the size of the ROI is smaller than the tissue sample.

In the tissue sample at least one ROI may be identified. In the tissue sample also more than one ROI may be identified. For example, the tissue sample may comprise two, three, four, five, ten or more ROIs. The different ROIs may be identified by different means, for example, some of ROIs are identified by image analysis software automatically, and a pathologist may also indicate ROIs manually. In a preferred embodiment at least one ROI is identified in the tissue sample, preferably two ROIs are identified in the tissue sample, more preferably more than two ROIs are identified in the tissue sample.

In a specific embodiment, the tissue sample may be cut into two layers. On one layer the labels for the imaging step are applied. Based on the image of this reference layer the ROI is selected and applied to the second layer (nucleic acid extraction slide). On the second layer the binding of oligonucleotide probes comprising the barcode sequence is carried out. The method has the advantage that imaging labels which are not compatible with the following steps of the protocol, e.g. binding of oligonucleotide probes, nucleic acid molecule extraction or sequencing can be used on the reference slide and therefore do not interfere with the reactions carried out on the second layer of the tissue sample (nucleic acid extraction slide).

The term "oligonucleotide probe", as used herein, denotes nucleic acid molecules comprising a barcode sequence.

Oligonucleotide probes may be for example RNA probes or DNA probes. Oligonucleotide probes comprising identical barcode sequences are referred to as a "species of oligonucleotide probes". Each species of oligonucleotide probes contains a unique barcode sequence. The barcode sequences may be designed or generated using random sequence generation. The designed or randomly generated sequences may be analyzed to ensure that the barcode sequences will not interfere with the capture of the nucleic acids. The barcode sequence may be ligated to the nucleic acids in the sample. The barcode sequence does not act as primer. The barcode sequence may have a size in the range of about 1-8 nucleotides.

The oligonucleotide probes may further comprise a "generic sequence". The generic sequence may be used to capture the nucleic acids in the sample by hybridizing to the nucleic acid to be targeted. In one embodiment, the generic sequence is used for selective amplification of nucleic acids in the sample. In such an embodiment the generic sequence is referred to as "primer sequence". The primer sequence is complementary to the nucleic acids in the sample that are to be targeted. For example, the primer sequence may comprise a poly-T sequence if the total mRNA of the sample is to be targeted or the primer sequence may comprise nucleotides complementary to a sequence stretch of a specific gene if only nucleic acids expressed by said gene are to be targeted. In an alternative embodiment, the generic sequence is used to ensure stable ligation of the barcode sequence to the nucleic acids in the sample, i.e. the generic sequence may be ligated to the nucleic acids in the sample to be targeted. In such an embodiment the generic sequence is referred to as "ligation sequence". In one embodiment the barcode sequence is ligated directly to the nucleic acids in the sample and no generic sequence is required. In one embodiment the oligonucleotide probe comprises at least one generic sequence. The generic sequence may have a size in the range of about 0 to 100 nucleotides, preferably 0 to 50 nucleotides, more preferably 0 to 30 nucleotides, even more preferably about 5 to 30 nucleotides.

The oligonucleotide probes may further comprise one or more "additional sequences". In one embodiment, an additional sequence may be used to enrich the nucleic acid ("enrichment sequence") or to purify the nucleic acid ("purification sequence"). In another embodiment, the additional sequence may be used to enrich and purify the nucleic acid. Additional sequences may also be sequences for the sequencing process, such as adapters used for next-generation sequencing, or sequences for selection or identification. In one embodiment, the additional sequence may be a sequence to which a primer aligns ("primer alignment sequence"). In embodiments where the oligonucleotide probes comprise a ligation sequence, the oligonucleotide probes may further comprise a primer alignment sequence. The primer sequence may be complementary to the primer alignment sequence.

The oligonucleotide probes may further comprise one or more spacer sequence, also referred to as spacer. The spacers may be arranged between the different sequence elements of the oligonucleotide probes. The spacer may have a size in the range of about 0 to 20 nucleotides. The oligonucleotide probes may be between about 15 to 150 nucleotides in length. In a preferred embodiment, the oligonucleotide probes are about 15 to 100 nucleotides in length, preferably about 20 to 50 nucleotides.

The oligonucleotide probes may be in a dried form or a liquid form. In a preferred embodiment, the oligonucleotide probes are in a liquid phase, preferably in a buffer solution or ink. Ink refers to any solution suitable for printing. In embodiments where the oligonucleotide probes are in a dried form, the oligonucleotide probes are dissolved before application.

In one embodiment the oligonucleotide probes bind to all DNA molecules in the sample. In a preferred embodiment, the oligonucleotide probes bind to all RNA molecules in the sample in order to provide a spatial map of the transcriptome. In another preferred embodiment the oligonucleotide probes only bind specific RNA molecules such as mRNA, rRNA, tRNA or other non-coding RNA, preferably the oligonucleotide probes specifically bind mRNA.

The term "allowing the oligonucleotide probes to bind to the nucleic acids of the sample" refers to the creation of nucleic acid-oligonucleotide probes complexes. The binding of the oligonucleotide probes to the nucleic acids of the sample can be achieved by different methods.

In one embodiment the oligonucleotide probes are ligated to the targeted nucleic acids in the sample. The ligation may occur via the barcode sequence or a generic sequence (the ligation sequence). Thus, in one preferred embodiment the binding of the oligonucleotide probes to the nucleic acids of the sample occurs via ligation. The oligonucleotide probes may be ligated to the target nucleic acid by any method known in the art. For example, ligation to mRNA may be via the poly-A tail, while ligation to DNA may be done after a digestion step producing sticky ends to which the oligonucleotide probes hybridize. In a specific embodiment the oligonucleotide probe comprises (i) a ligation sequence, (ii) a barcode sequence and optionally (iii) one or more additional sequences. The different sequences may be separated by spacers. Further, additional sequences may also be located between the ligation sequence and the barcode sequence. If the targeted nucleic acid is to be amplified, a primer alignment sequence is present. Thus, in another specific embodiment the oligonucleotide probe comprises (i) a ligation sequence, (ii) a barcode sequence and (iii) a primer alignment sequence. The oligonucleotide probe may comprise spacers and/or further additional sequences. The sequences are arranged within the oligonucleotide probe in such a way that in an amplification or reverse transcription reaction the barcode is incorporated into the amplified DNA or cDNA, respectively. In another preferred embodiment the oligonucleotide probe comprises a barcode sequence that is ligated to the nucleic acid which may be followed by one or more generic and/or additional sequence.

In an alternative embodiment the oligonucleotide probe comprises a primer sequence. In this scenario amplification and/or reverse transcription of the nucleic acid is required. Thus, in one preferred embodiment the binding of the oligonucleotide probes to the nucleic acids of the sample occurs via hybridization, wherein the oligonucleotide probes are used as primers for amplification or reverse transcription. In embodiments where the oligonucleotide probe acts as primer the oligonucleotide probe comprises (i) a primer sequence, (ii) a barcode sequence and optionally (iii) one or more additional sequences, wherein the primer sequence acts as primer for an amplification or reverse transcription reaction. The oligonucleotide probes may comprise spacers and/or further additional sequences. The sequences are arranged within the oligonucleotide probe in such a way that in an amplification or reverse transcription reaction the barcode is incorporated into the amplified DNA or cDNA, respectively.

It is to be understood that the binding of the oligonucleotide probes to the nucleic acids in the sample is not restricted to the above described embodiments and may occur via numerous other ways. For example, generic primer alignment sequences may be ligated to the targeted nucleic acids and the oligonucleotide probes may be used as primers in an amplification or reverse transcription reaction. Another example may be ligation to nucleic acids, such as to sticky ends of DNA after digestion, onto which in a second ligation reaction an oligonucleotide probe is ligated. The skilled person would be aware of the different molecular technique to capture the nucleic acids to be targeted and different options to incorporate the barcode sequence.

The binding of the oligonucleotide probes to the nucleic acids in the sample encompasses the binding of one or more species of oligonucleotide probes to nucleic acid molecules in a predefined location within the ROI. In one embodiment, one species of oligonucleotide probes is applied onto each predefined location within the ROI. Thus, in a specific embodiment one species of oligonucleotide probes binds to one targeted nucleic acid molecule in one predefined location. This approach is preferred for a small number of predefined locations or low resolution approaches.

In another embodiment at least two different species of oligonucleotide probes are applied onto one predefined locations within the ROI. Thus, in a specific embodiment at least two different species of oligonucleotide probes bind to one targeted nucleic acid molecule in one predefined location. This approach allows a high spatial resolution mapping of complex molecular profiles that efficiently uses multiplexing ROIs per sample. In one specific embodiment at least one of the species of oligonucleotide probes that binds to one nucleic acid molecule binds via ligation via its barcode sequence. In another specific embodiment at least one of the species of oligonucleotide probes that binds to one nucleic acid molecule comprises a generic sequence, wherein optionally the generic sequence is complementary to the targeted nucleic acid. For example, one species of oligonucleotide probes may comprise a ligation sequence and a second species of oligonucleotide probes may comprise a primer sequence for amplification or reverse transcription of the nucleic acid. In another example, one species of oligonucleotide probes may not comprise a generic sequence and a second species of oligonucleotide probes may comprise a generic sequence; thus the oligonucleotide probe without generic sequence may bind to a nucleic acid molecule via ligation via its barcode sequence and the oligonucleotide probe with a generic sequence may bind via hybridization via its primer or ligation sequence. In another embodiment at least one of the species of oligonucleotide probes that binds to one nucleic acid molecule comprises an additional sequence, wherein the additional sequence is a purification sequence or a primer alignment sequence. For example, one species of oligonucleotide probes may comprise a ligation sequence and a purification sequence and a second species of oligonucleotide probes may comprise a primer sequence. In another example, one species of oligonucleotide probes may not comprise a generic sequence but an additional sequence and a second species of oligonucleotide probes may only comprise a generic sequence; thus the oligonucleotide probe without generic sequence may bind to a nucleic acid molecule via ligation via its barcode sequence and comprise a primer alignment sequence onto which a forward primer hybridizes and the oligonucleotide probe with a generic sequence may bind via hybridization, wherein the generic sequence acts as reverse primer. It is to be understood that the combinations of sequences within one species of oligonucleotide probes is not restricted to the above described embodiments. The skilled person would be aware that numerous other combinations are possible for capturing the nucleic acids to be targeted and marking them with a corresponding barcode. Thus, further combinations of sequences within one species of oligonucleotide probes when combined with at least one further species of oligonucleotide probes that are suitable to effectively mark the targeted nucleic acid are explicitly encompassed.

The "predefined location" onto which oligonucleotide probes are applied represents one or more positions within the ROI. Depending on the question of the investigator, the whole ROI may be divided into separate predefined locations, i.e. one predefined location is right next to another predefined location so that they share a border, or parts of the ROI may be selected, i.e. the predefined location within the ROI may represent islets separated by regions in the ROI onto which no probes are applied. Preferably the predefined locations refer to more than one position within the ROI.

In one embodiment the predefined locations within the ROI are systematically arranged, for example in rows and columns. In one embodiment, the ROI comprises at least 1, 2, 5, 10, 50, 100, 500, 750, 1000, 1500, 3000, 5000, 10000, 20000, 40000, 50000, 75000, 100000, 150000, 200000, 300000, 400000, 500000, 750000, 800000, 1000000 or more predefined locations. In a preferred embodiment the ROI comprises at least 1, 2, 5, 10, 20, 30, 40, 50 or 100 predefined locations, preferably the ROI comprises at least 10 predefined locations. In another embodiment, the area of each predefined location may be about 1 $\mu m^2$, 2 $\mu m^2$, 3 $\mu m^2$, 4 $\mu m^2$, 5 $\mu m^2$, 10 $\mu m^2$, 12 $\mu m^2$, 15 $\mu m^2$, 20 $\mu m^2$, 50 $\mu m^2$, 75 $\mu m^2$, 100 $\mu m^2$, 150 $\mu m^2$, 200 $\mu m^2$, 250 $\mu m^2$, 300 $\mu m^2$, 400 $\mu m^2$, or 500 $\mu m^2$. To each predefined location a unique species of oligonucleotide probes or a unique combination of two or more different species of oligonucleotide probes is applied. If two or more species of oligonucleotide probes are applied, it is preferred that a different species of oligonucleotide probes is applied to each row and a different species of oligonucleotide probes is applied to each column. For example, row 1 comprises one species of oligonucleotide probes that is different from the species of oligonucleotide probes in row 2 that in turn is different from the oligonucleotide probes in row 3 etc. Column A comprises a species of oligonucleotide probes that is different from any of the species of oligonucleotide probes applied in the rows, column B comprises again a further different species of oligonucleotide probes etc. The predefined location in column A, row 1 (A1) has thus a unique combination of oligonucleotide probes that is different from the combination of A2, B1 or B2 etc. Using this approach fewer species of oligonucleotide probes need to be employed reducing the costs of the assay. Further species of oligonucleotide probes may be added, for example addition of different species of oligonucleotide probes in diagonals or to freely defined predefined locations such as sub-ROIs. In a preferred embodiment a unique combination of at least two species of oligonucleotide probes are applied to each predefined location, preferably a unique combination of two species of oligonucleotide probes.

In an alternative embodiment the predefined locations within the ROI are defined freely. The free arrangement of predefined locations has the advantage that further sub-regions of interest (sub-ROI) within the ROI can be defined without any restrictions. Thus, compared to the conventional arrangement of arrays in columns and rows with regular features of equal sizes, the free arrangement allows for predefined locations of any shape and size and different predefined locations with different shapes and sizes. For example, in a tissue sample a ROI may be identified based on the presence of a particular cell type. Within said ROI further sub-ROIs may be identified based on morphological features. These sub-ROIs may form distinct isles within the ROI having different shapes and sizes. The predefined locations within the ROI may be defined such that each sub-ROI represents a separate predefined location. In such a scenario, the remaining ROI minus the regions covered by the sub-ROIs may be of no interest and no oligonucleotide probes are applied onto this region, or it may represent a further predefined location, or it may be further divided into predefined locations by systematical arrangement of rows and columns. To each predefined location a unique species of oligonucleotide probes or a unique combination of two or more species of oligonucleotide probes may be applied. Sub-ROIs representing separate predefined locations may be distinct from one another or may partially overlap. In cases where sub-ROIs partially overlap, the region of overlap would be identifiable by the unique combination of the at least one species of oligonucleotide probes specific for a first sub-ROI and the at least one species of oligonucleotide probes specific for a second sub-ROI. In one embodiment at least two sub-ROIs overlap partially. In another embodiment more than two sub-ROIs overlap partially. In yet another embodiment the sub-ROIs do not overlap. Any information can be used to identify sub-ROIs and the identification of sub-ROIs is not restricted to information obtained by identification of the ROI. Features that may be used to identify a sub-ROI include, but are not limited to, cell type, morphology, color, transparency, presence/absence of specific molecules such as, for example, antibodies, cytokines or drugs, or the application of radiation to specific areas of the tissue sample before it was taken from the patient.

In a further embodiment, the predefined locations are defined by application of a mask. The mask may be a "separation mask". A separation mask may have any pattern to mark the ROI. In one embodiment the separation mask is a "lattice separation mask" providing rows and columns for a systematic positional characterization of the ROI (FIG. 1). In another embodiment the separation mask may be a "freeform separation mask" based on the shape of the ROI and sub-ROIs (FIG. 1). In another embodiment the separation mask may be a combination of a lattice separation mask and a freeform separation mask as exemplary shown in FIG. 1.

The separation mask may be applied in different ways. In one embodiment the separation mask defines the predefined regions by providing a full trench that is applied through the entire thickness of the tissue sample ("full separation mask"), preferably by scratching, laser ablation or by creating physical barriers such as a metal grid. In another embodiment the separation mask defines the predefined regions by providing a top barrier ("top separation mask"). The top separation mask may define the predefined locations by physical barriers. The top separation mask may also define the predefined areas by a structuring process that confines reagents in the desired area ("positional mask"), preferably by topological constraints or by patterning the wettability of the tissue locally. Lithographic techniques can be employed to structure such layers. In a preferred embodiment the surface of the ROI is structured with a self-assembled monolayer (SAM) on a thin gold layer that is evaporated on the surface of the ROI. The SAM layer may be applied by micro-contact printing of an organic thiol that is used as an etch resist in the etching of the gold layer. The SAM is hydrophobic and prevents the spreading of the oligonucleotide probes during inkjet printing. The top separation mask may also be printed on top of the ROI, wherein the ink acts as physical barrier. FIG. 1 shows in the side views exemplarily a top separation mask 5 and a full separation mask 6. In one embodiment the predefined locations are defined by a separation mask. In a preferred embodiment the separation mask is a top separation mask, optionally printed onto the sample, or a full separation mask, wherein the separation mask is a lattice separation mask, a freeform separation mask or a combination thereof. In a more preferred embodiment the separation mask is a top separation mask applied by printing. Inkjet printing of a wax with a heated inkjet print head can be used or inkjet printing with a UV curable ink. Both are well-known techniques in the graphics industry.

Top masks can also be applied as a pre-manufactured integral part, like a micro-titer plate with open base. The micro-titer plate could be a 384 well plate or a 1536 well plate, or any other number when manufactured for this purpose. The well plate can be clamped on the tissue sample to ensure good physical contact between the plastic walls of the well plate and the tissue sample. Then oligonucleotide probes can be added dissolved in a buffer in each well that overlaps with the predetermined ROI. Each well can receive a different ink, i.e. a different oligonucleotide probe. Multiple depositions are possible to provide all reagents. Inkjet printing or micro-dosing can be used to provide the reagents to the wells. The height of the walls of such a top mask is of the order of 0.5 to 5 mm. This means that the dispensed volume in each well can be of the order of 100 nL to 10 µL, more preferably 0.5 to 2 µL.

In another embodiment no separation mask (be it a physical, chemical or mechanical mask) is used and the predefined locations are defined by the local application of the oligonucleotide probes such that they do not intermix between different predefined locations on the sample. In one embodiment, the oligonucleotide probes are applied using printing inks that do not spread readily or in which the volume is kept small enough to maintain the desired spatial resolution, wherein the printing pattern defines the predefined locations. In this embodiment the application of the oligonucleotide probes and defining the predefined locations occur simultaneously. The ink may be gelated after application to ensure fixation on the desired position, while the oligonucleotide probes are still able to diffuse into the ROI of the tissue sample. State of the art liquid transfer technologies may be used to apply the oligonucleotide probes in a specific pattern on the ROI. In one embodiment the oligonucleotide probes are applied onto the predefined locations by liquid transfer technologies, preferably by contact printing techniques or non-contact printing techniques, such that the applied oligonucleotide probes do not intermix between different predefined locations. In a preferred embodiment the liquid transfer technology is a contact printing technique, preferably dip-pen plotting or micro-contact printing. In another preferred embodiment the liquid transfer technology is a non-contact printing technique, preferably inkjet. In one embodiment oligonucleotide probes are printed in horizontal lines or in dots positioned in a horizontal line (representing rows). Then a vertical movement is used to print oligonucleotide probes in vertical lines or positioned on top of the dots already present (representing columns). Multi-nozzle printers can be used that can print different printing inks simultaneously. Thermal inkjet or piezo-driven inkjet heads can be used. Piezo-driven printers are preferred to avoid possible degradation of the proteins in the printing ink. The liquid transfer technology of choice may be adapted based on the resolution desired. In another embodiment the oligonucleotide probes are printed according to the shapes of identified sub-ROIs.

The printing ink contains oligonucleotide probes dissolved in a solvent, like water or a saline buffer, optionally with surfactants and stabilizers. Concentrations of the oligonucleotide probes in the ink can be in the range between 1 nM to 1 mM, preferably between 100 nM and 10 µM. Different oligonucleotides can be dissolved in the same ink. Preferably also enzymes are dissolved in the same ink. For stability of enzymes BSA or other sera can be added in concentrations that are typical for stable storage, e.g. between 0.5 and 5% w/w.

Printing volumes are chosen typical for the deposition technique used and depending on the spatial resolution that is desired. For inkjet printing the printing volume can be in the range between 50 pL and 5 µL, more preferably between 100 pL and 1 µL. For dip-pen plotting the transferred volume depends on the pen size and residence time. Typical volumes that are transferred are in the range between 1 pL and 1 µL, preferably between 10 pL and 100 nL.

The application of the oligonucleotide probes as described for embodiments in which no separation mask is used may also be used for embodiments in which the predefined locations are defined by a separation mask. For example, in a first step the separation mask may be printed defining predefined locations and in a second step the oligonucleotide probes may be applied by printing onto the predefined locations. Thus, in one embodiment the oligonucleotide probes are applied by printing. In another embodiment the oligonucleotide probes are applied by a different method than printing such as pipetting.

Oligonucleotide probes may also be prepared in a gel-like layer or gel-layer, wherein this layer is applied onto the predefined locations within the ROI. The gel layer may be applied in a single step on the ROI and the oligonucleotide probes are transferred to the ROI by diffusion. The term "gel-like" or "gel", as used herein, denotes a solid, jelly-like material that can have properties ranging from soft and weak to hard and tough, in which the oligonucleotide probes are able to diffuse from the gel into the ROI. Thus, in one embodiment the oligonucleotides probes are in the form of a gel layer or gel-like layer that is applied onto the sample.

Oligonucleotide probes may also be applied in a separate disposable (e.g. with small wells, like a well plate) which will be connected later on to the ROI. This approach has the advantage that it can be manufactured offline, including relevant quality control measures to check if all liquids have been deposited. Deposition of the oligonucleotide probes in a separate disposable offline makes the use of liquid transfer equipment in the pathology lab obsolete. In one embodiment, the ROI can be pressed into a well plate as described in Armani et al., 2009, Lab Chip 9(24): 3526-3534 and Armani et al., 2011, Anal Bioanal Chem 400: 3383-3393. Oligonucleotide probes or a unique combination of oligonucleotide probes may be added to the bottom of each of the wells by spotting. The oligonucleotide probes may be dried prior to use.

Oligonucleotide probes may also be applied by a combination of the above described means and/or a combination of using no separation mask and a separation mask. For example, in a first step oligonucleotide probes may be printed onto different sub-ROIs thereby defining the predefined locations without the use of a separation mask and in a second step oligonucleotide probes may be applied by pipetting onto predefined locations defined by a top separation mask. Thus, the oligonucleotide probes may be applied sequentially or simultaneously. It is to be understood that numerous further combinations are possible and the application of oligonucleotide probes is not restricted to the above described embodiments.

In embodiments where more than two species of oligonucleotide probes are applied onto predefined locations within the ROI, the application may be sequential. For example, oligonucleotide probes that are to be ligated to a nucleic acid molecule may be applied in a first step, providing conditions under which the probes are ligated to the nucleic acid molecules, and in a second step oligonucleotide probes hybridizing to the nucleic acid molecules and/or the oligonucleotide probe ligated to the nucleic acid molecules may be applied. Thus, in one embodiment different species of oligonucleotide probes are applied onto the predefined locations within the ROI sequentially. In another embodiment different species of oligonucleotide probes are applied onto the predefined locations within the ROI simultaneously.

In a preferred embodiment the oligonucleotide probes are applied in a liquid phase onto the predefined locations within the ROI. In a further preferred embodiment the oligonucleotide probes are applied in a liquid phase onto the predefined locations within the ROI, wherein the predefined locations were identified taking into account tissue information. In a further preferred embodiment the oligonucleotide probes are applied in a liquid phase with high ionic strength to enable hybridization to the target molecules. In another preferred embodiment the oligonucleotide probes are applied in a liquid phase that gelates immediately after application to the sample, either by a temperature step or radiation that is applied. This can be achieved by adding polymers, like poly-acrylamide that undergo thermo-reversible gelation in solution and/or adding monomers that can polymerize under irradiation and in this way lead to gelation. The gelation should avoid possible intermixing of the probes at different predefined locations.

The nucleic acid molecules in the ROI may be pre-treated. In one embodiment, the nucleic acids of the sample are pretreated in order to target the right type of nucleic acid molecules and/or for efficient ligation of oligonucleotide probes. In embodiments where the nucleic acids to be targeted are DNA molecules, the pretreatment may encompass digestion of the DNA to provide DNA fragments of smaller size according to methods well known in the art.

After the application of the oligonucleotide probes onto predefined locations within the ROI, the oligonucleotide probes diffuse into the ROI. The size of the oligonucleotide probes allows for a deep penetration of the tissue sample in a short time. The oligonucleotide probes within their predefined locations of the ROI then bind to the nucleic acids of the sample thereby creating nucleic acid-oligonucleotide probes complexes. The term "nucleic acid-oligonucleotide probes complex", as used herein, denotes a complex of the nucleic acid to be detected and at least one oligonucleotide probe. The nucleic acid to be detected may be in a complex with more than one species of oligonucleotide probe, for example, with two species of oligonucleotide probes. During the process of diffusion and binding a humid atmosphere is provided at the surface to avoid evaporation of the solvents. A temperature step may be applied during that period to achieve a good conversion of the reactions. The separation mask may stay in place during that step or optionally be removed after the application of the probes. An elevated temperature accelerates diffusion and binding reactions. The temperature should be kept below the melting temperature of the probes in the case hybridization is used for binding. Alternatively the temperature should be chosen such that the ligase performs well. In a preferred embodiment the temperature is in the range between about 20 and 45° C., preferably between about 30 and 40° C.

After the binding of the oligonucleotide probes to the nucleic acids of the sample, the nucleic acid-oligonucleotide probes complexes are extracted from the ROI. In one embodiment the extraction is performed by immersion of the ROI in an extraction buffer at elevated temperature. Extraction buffers common in sample preparation for molecular assays and known in the art may be used. The extracted nucleic acids may be collected in a single tube for further analysis. The solution of extracted nucleic acid-oligonucleotide probes complexes is referred to as the spatial molecular profile (SMP) extract.

In one embodiment, the extracted nucleic acids are purified by methods known in the art. In another embodiment, the extracted nucleic acids are enriched by methods known in the art. In a further embodiment, the extracted nucleic acids are purified and enriched.

In yet a further embodiment, DNA molecules are generated from the extracted nucleic acid-oligonucleotide probes complexes via DNA amplification, optionally wherein the generation of DNA molecules occurs after a reverse transcription reaction. In a preferred embodiment, the extracted nucleic acids are RNA molecules that are reverse transcribed and amplified.

Nucleic acid amplification may be achieved by means of a cyclic amplification. The cyclic amplification may comprise any number of amplification cycles that is equal or greater than two. Usually, cyclic amplification reaction comprises at least 10 or at least 20 cycles. An exemplary cyclic amplification is a polymerase chain reaction (PCR). PCR is an established standard method in molecular biology that is described, for example, in detail in Sambrook et al., supra. Typically, PCR is used for the amplification of double-stranded DNA molecules by employing a thermostable DNA polymerase. In a preferred embodiment the nucleic acid amplification is a cyclic amplification, preferably a PCR.

In alternative embodiments nucleic acid amplification is achieved by means of an isothermal amplification method. Amplifying nucleic acids in isothermal conditions makes it possible to avoid the use of a thermocycling apparatus. There are several types of isothermal nucleic acid amplification methods known to the skilled person, including nicking enzyme amplification reaction, transcription-mediated amplification, nucleic acid sequence-based amplification, signal-mediated amplification of RNA technology, strand displacement amplification, rolling circle amplification, loop-mediated isothermal amplification, isothermal multiple displacement amplification, helicase-dependent amplification, single primer isothermal amplification, and circular helicase-dependent amplification. Isothermal nucleic acid amplification technologies are reviewed, e.g., in P. Gill and A. Ghaemi, 2008, Nucleosides Nucleotides Nucleic Acids 27(3):224-243.

If the nucleic acid is RNA, the generation of DNA molecules further comprises subjecting the nucleic acids to reverse transcription prior to subjecting them to amplification. Reverse transcription is another standard method in molecular biology and also described, e.g., in Sambrook et al., supra.

After the nucleic acid-oligonucleotide probe complex is extracted, and optionally subjected to any of the methods described above, the SMP extract is sequenced. The term "sequencing the extracted nucleic acid molecules", as used herein, is to be understood in a broad sense, i.e. refers to any method that provides sequence information. For example, sequence information may be obtained by hybridization with specific probes or microarrays. In one embodiment sequencing the extracted nucleic acid molecules refers to the sequencing of DNA molecules, optionally obtained from RNA by reverse transcription. Methods suitable for sequencing DNA molecules are known in the art and include, but are not limited to, Sanger sequencing, pyrosequencing or next generation sequencing (NGS). In another embodiment sequencing the extracted nucleic acid molecules refers to the sequencing of RNA molecules by nanopore sequencing, microRNA sequencing or whole transcriptome shotgun sequencing. In a preferred embodiment the sequencing is DNA sequencing, preferably NGS.

Where the sequence information is obtained by NGS, in embodiments where the oligonucleotide probes act as primers in NGS, the oligonucleotide probes comprise as additional sequence a NGS adapter.

After the sequence information of the sequenced nucleic acid molecules has been obtained, the sequenced nucleic acid molecules are correlated to the initial location of the corresponding targeted nucleic acid molecules within the ROI to generate a spatial distribution of the targeted nucleic acid molecules. Thus, a spatial two-dimensional map is created where the sequenced nucleic acids are shown according to the predefined locations, e.g. defined by a separation mask, from which they originated. Thus, in one embodiment the sequenced nucleic acid molecules are correlated to the initial location of the corresponding targeted nucleic acid molecules within the predefined location within the ROI to generate a spatial distribution of the targeted nucleic acid molecules, wherein each location is identified by one or more species of oligonucleotide probes bound to the nucleic acids of the sample in predefined locations within the ROI. In another embodiment the unique combination of at least two different species of oligonucleotide probes is used to identify the location of the targeted nucleic acid molecules within the ROI. The extracted and sequenced nucleic acid molecules comprise the barcode sequence of the oligonucleotide probes that bound to the target nucleic acids of the sample in a predefined location within the ROI. Since to each predefined location within the ROI a unique species of oligonucleotide probes or a unique combination of oligonucleotide probes was applied which bound the target nucleic acids of the sample, the extracted and sequenced nucleic acid molecules encompass the barcode sequence of the oligonucleotide probes. Each nucleic acid molecule may be correlated based on the barcode sequence it comprises to the predefined location onto which the species of oligonucleotide probes comprising said barcode sequence was applied. The resulting correlation provides a spatial map showing the initial locations of the targeted nucleic acids within the ROI. Such a spatial map may, for example, provide information on the expression status, the mutation status, the degradation status, the methylation status, the epigenetic status of the nucleic acids, or combinations thereof.

In one embodiment, the spatial distribution of the targeted nucleic acid molecules may be correlated with an image of the ROI or with an image of the tissue sample in which the ROI was identified. The spatial distribution of the targeted nucleic acid molecules may be visualized providing a two-dimensional spatial map. In one embodiment the spatial distribution of the targeted nucleic acid molecules is correlated to spatial patterns of an image obtained from the ROI. Thus, in one embodiment, the method provides a two-dimensional spatial map to visualize the spatial distribution of the targeted nucleic acid molecules. In a further embodiment, the method further comprises overlaying the two-dimensional spatial map with the image of the ROI or with the image of the tissue sample in which the ROI was identified. An image of the ROI may be obtained before or after identification of the ROI. Thus, in one embodiment an image is obtained from the tissue sample before identifying at least one ROI. In another embodiment an image of the tissue is obtained after identifying at least one ROI. In yet another embodiment an image is obtained from the ROI before or after applying the oligonucleotide probes onto the predefined locations within the ROI. The images may be obtained by any method known in the art such as digital pathology or a microscope with a camera. In one embodiment, the spatial distribution of the targeted nucleic acid molecules is correlated with the predefined locations located within the ROI and defined by a separation mask, wherein the image is obtained after applying the separation mask and before or after applying the oligonucleotide probes onto the predefined locations within the ROI, preferably before application of the oligonucleotide probes. In a preferred embodiment, the spatial distribution of the targeted nucleic acid molecules is correlated with an image of the ROI obtained before or after applying the oligonucleotide probes onto the predefined locations within the ROI, preferably before application of the oligonucleotide probes. In another preferred embodiment, the spatial distribution of the targeted nucleic acid molecules is correlated with an image of the ROI obtained after applying a separation mask and before applying the oligonucleotide probes onto the predefined locations defined by the separation mask.

The spatial map can be visualized for instance by displaying false colors, with each predefined locations as defined by a grid representing an area of the same color. The spatial map can be overlaid with an image of the ROI or with an image of the tissue sample. For example, the spatial map is configured as a semi-transparent image and is overlaid on the image of the ROI or with the image of the tissue sample. Or vice-verse, the image of the ROI or the image of the tissue sample is configured as a semi-transparent image and is overlaid on the spatial map. In a preferred embodiment the number or amount of the same targeted nucleic acid molecules determined in the assay with the same species of oligonucleotide probes is related to the color of the map in the corresponding predefined location. In another embodiment a particular combination of targeted nucleic acid molecules, like for instance a subset of those carrying a known oncogenic mutation, is correlated to the color. In yet another embodiment the overexpression of a particular set of targeted nucleic acid molecules related to specific genes can be correlated to the color on the map. It is to be understood that many different profiles can be defined and related to a way of visual display, depending on the biological and/or clinical question that is addressed. Instead of or in combination with colors other annotations can be displayed in a spatial map.

The correlation of the spatial distribution of the targeted nucleic acid molecules to the spatial patterns of the initial image, i.e. the spatial map, may be used to answer a clinical question and provide guidance for a clinical decision. The results obtained by a spatial map created by the method of the invention may be used for clinical diagnosis or monitoring of a clinical response in a patient. The correlation of the spatial distribution of the targeted nucleic acid molecules to the spatial patterns of the initial image may also be used in the field of research.

In a preferred embodiment the tissue sample and/or ROI are imaged. An image taken of a tissue sample may be used to identify the region of interest as well as the spatial resolution of the pattern based on the image-based analysis of the tissue before the application of the reagents.

Another aspect of the invention relates to a reaction ligating 5'-oligonucleotide probes and 3'-oligonucleotide probes to the 5'-end and the 3'-end of the RNA molecule and simultaneously applying a DNA molecule introducing a restriction site on the ligation site of the oligonucleotide probe dimer and a restriction enzyme that is suitable to cleave the restriction site, wherein the 5'-end and 3'-end of the DNA molecule are modified so that they are not participating in the ligation reaction. Thereby the dimers that occur between the oligonucleotide probes when they react with each other (i.e. oligonucleotide probe dimer) are cleaved into fully active individual 5'-oligonucleotide probes and 3'-oligonucleotide probes. The cleaved oligonucleotide probes can be reused in the ligation reaction in order to be ligated to the 5'-end and 3'-end of the RNA molecule.

A specific embodiment relates to the ligation reaction on a FFPE tissue sample, ligating 5'-oligonucleotide probes and 3'-oligonucleotide probes to the 5'-end and the 3'-end of the RNA molecule and simultaneously applying a DNA molecule introducing a restriction site on the ligation site of the oligonucleotide probe dimer and a restriction enzyme that is suitable to cleave the restriction site, wherein the 5'-end and 3'-end of the DNA molecule are modified so that they are not participating in the ligation reaction.

Figure 2A:
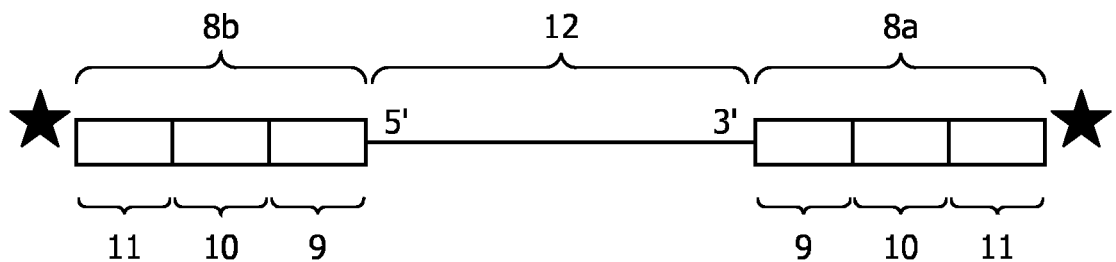
FIG. 2 (A) Exemplary composition of oligonucleotide probes that bind via ligation. Two species of oligonucleotide probes 8a and 8b comprising a generic sequence 9, barcode sequence 10a and 10b, respectively and additional sequence 11 bound to a nucleic acid 12 are shown. (B) Standard oligonucleotide probe ligation reaction scheme (adapted from http://rnase.uoregon.edu/#library-prep-addition-of-adapters-via-ligation). The nucleic acid is fragmented RNA. In a first step one species of oligonucleotide probe is ligated to the 3'-end of the RNA. In a second step another species of oligonucleotide probe is ligated to the 5'-end of the RNA. In a third step cDNA is generated via a reverse transcription reaction, wherein the primer comprising a sequence for next-generation sequencing (NGS-adapter) hybridizes to the primer alignment sequence of the oligonucleotide probe. In a fourth step the cDNA is amplified by PCR.
Figure 2B:
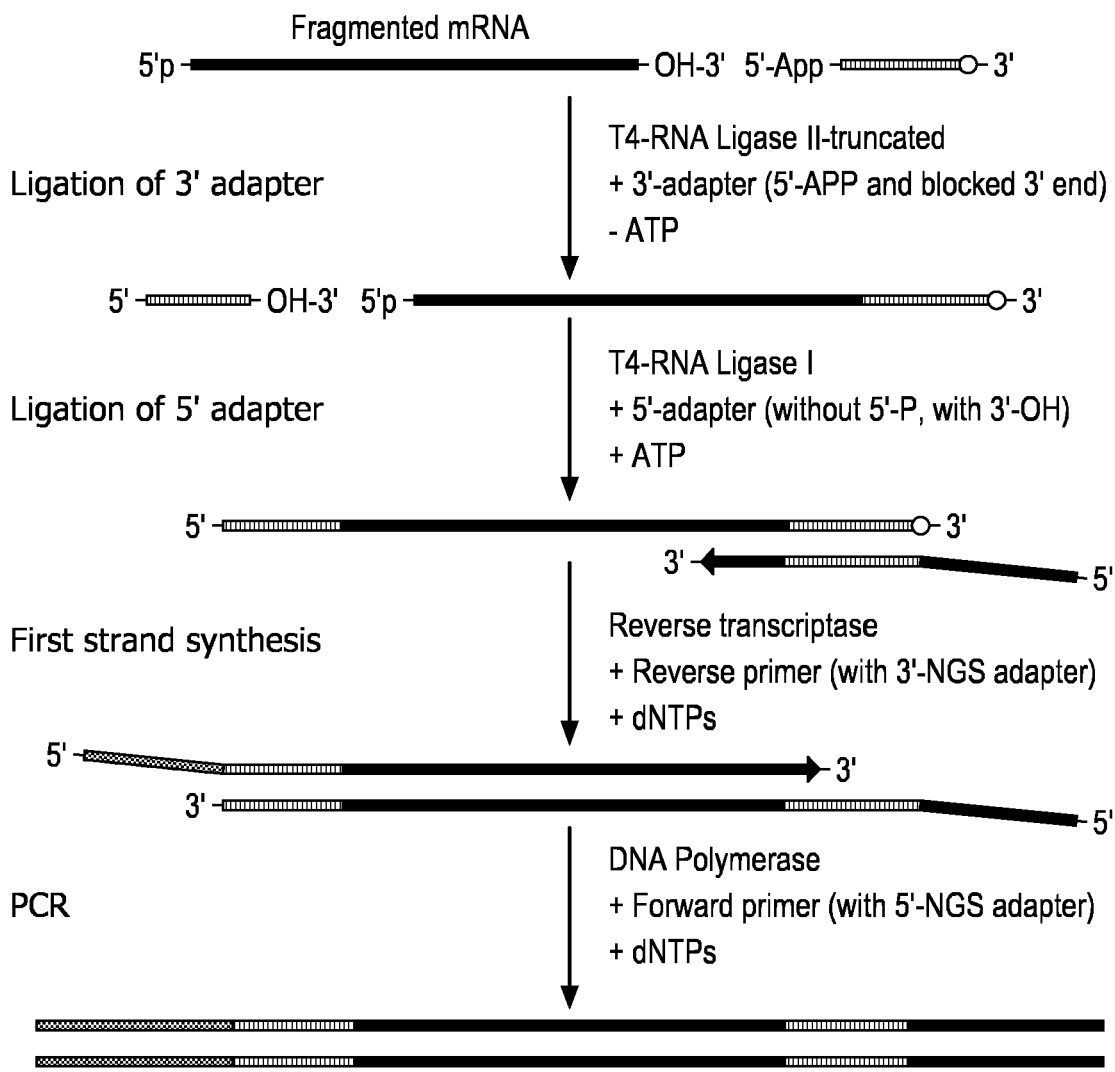
Figure 3:
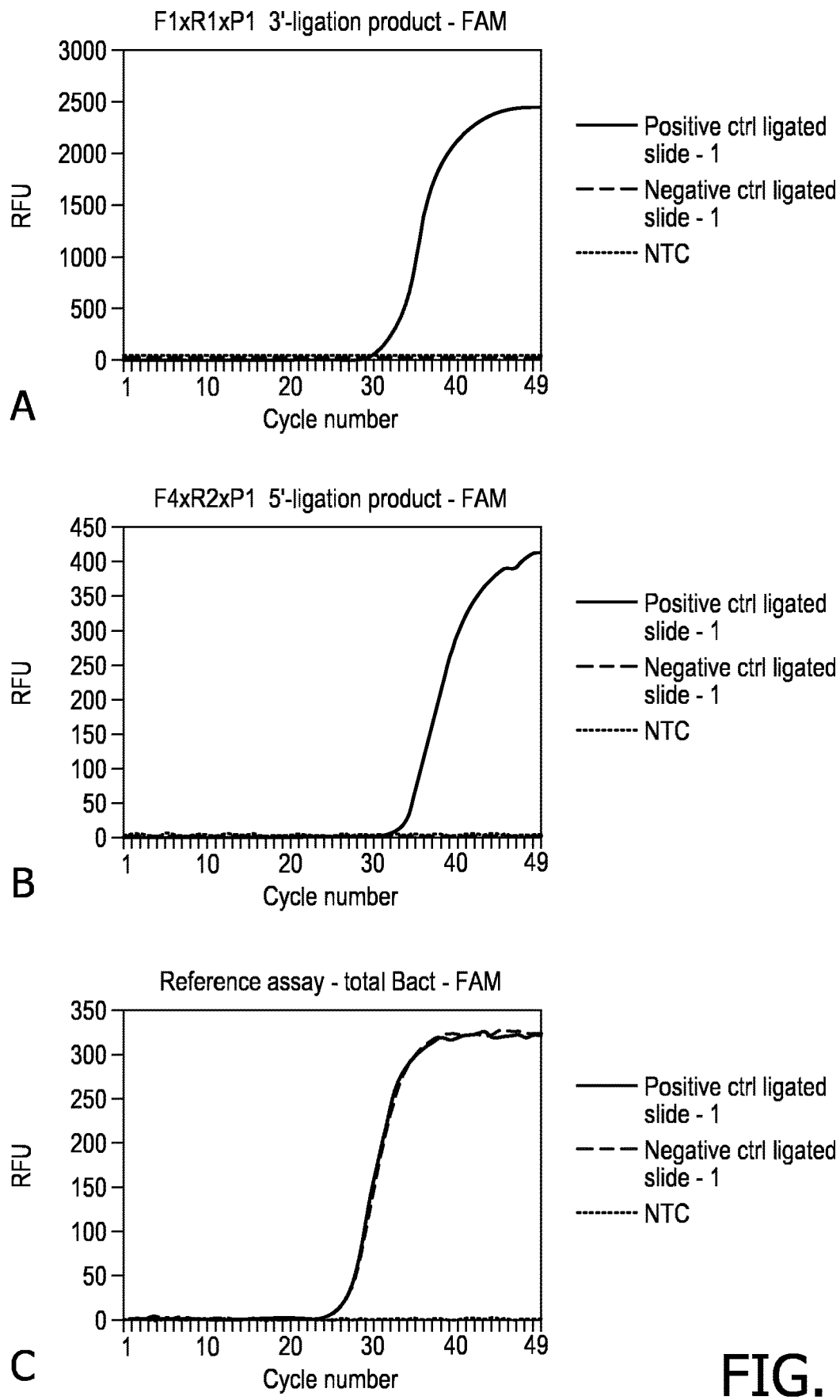

In the standard oligonucleotide probe ligation reaction scheme as set out in FIG. 2B the ligation reaction is quenched by a reverse transcription reaction thereby avoiding the formation of oligonucleotide probe dimers. The reverse transcription reaction is rather inefficient on a FFPE tissue sample. In the oligonucleotide probe ligation protocol of the invention the oligonucleotide probe dimer is cleaved by the restriction enzyme, thus the reverse transcription reaction step can be avoided on the FFPE tissue sample. Further, using the protocol of the invention the T4 RNA ligase I and II reactions can be combined in one step, as described in the Examples and FIG. 3. Thus the oligonucleotide probe ligation reaction method of the invention is advantageous over the prior art.

In a specific embodiment the invention relates to a ligation reaction ligation 5'-oligonucleotide probes and 3'-oligonucleotide probes to the 5'-end and the 3'-end of the RNA molecule and simultaneously applying a DNA molecule introducing a HaeIII restriction site on the ligation site of the oligonucleotide probes dimer and a HaeIII restriction enzyme cleaving at the restriction site.

The above described ligation reaction can be used in step b) of the method for spatial detecting RNA molecules in a tissue sample as described herein.

In particular, the above described ligation reaction can be used in step b) of the method for spatial detecting RNA molecules in a FFPE tissue sample as described herein. Thereby it can be avoided that the reverse transcription reaction has to be carried out on the FFPE tissue sample. This method is advantageous as it avoids the reverse transcription reaction which is rather inefficient to the FFPE sample. Further, using this protocol T4 RNA ligase I and II reactions can be combined in one step.

In a specific embodiment the method of spatial detecting nucleic acids in a tissue sample comprises the steps of:
a1) acquiring an image of the tissue sample;
a2) identifying at least one ROI within the sample;
a3) applying a mask to the ROI including different predefined locations;
b) applying at least one species of oligonucleotide probes onto the predefined locations within the ROI and allowing the oligonucleotide probes to bind to the nucleic acids of the sample, wherein the oligonucleotide probes comprise a barcode sequence;
c) extracting the nucleic acid-oligonucleotide probe complexes;
d) sequencing the extracted nucleic acid molecules;
e) correlating the sequenced nucleic acid molecules to the initial location of the corresponding target nucleic acid molecule within the ROI to generate a spatial distribution of the targeted nucleic acid molecules; wherein each location is identified by one or more species of oligonucleotide probes bound in step b).

In another specific embodiment the method of spatial detecting nucleic acids in a FFPE tissue sample comprises the steps of:
a1) deparaffinizing the FFPE tissue sample;
a2) acquiring an image of the tissue sample;
a3) identifying at least one ROI within the sample;
a4) applying a mask to the ROI including different predefined locations;
b) applying at least one species of oligonucleotide probes onto the predefined locations within the ROI and allowing the oligonucleotide probes to bind to the nucleic acids of the sample, wherein the oligonucleotide probes comprise a barcode sequence;
c) extracting the nucleic acid-oligonucleotide probe complexes;
d) sequencing the extracted nucleic acid molecules;
e) correlating the sequenced nucleic acid molecules to the initial location of the corresponding target nucleic acid molecule within the ROI to generate a spatial distribution of the targeted nucleic acid molecules; wherein each location is identified by one or more species of oligonucleotide probes bound in step b).

In a specific embodiment the method of spatial detecting RNA in a tissue sample comprises the steps of:
a1) acquiring an image of the tissue sample;
a2) identifying at least one ROI within the sample;
a3) applying a mask to the ROI including different predefined locations;
b) applying at least one species of oligonucleotide probes onto the predefined locations within the ROI and allowing the oligonucleotide probes to bind to the RNA molecules of the sample, wherein the oligonucleotide probes comprise a barcode sequence;
c) extracting the RNA-oligonucleotide probe complexes;
d) sequencing the extracted RNA molecules;
e) correlating the sequenced RNA molecules to the initial location of the corresponding target RNA molecule within the ROI to generate a spatial distribution of the targeted RNA molecules; wherein each location is identified by one or more species of oligonucleotide probes bound in step b).

In a specific embodiment the method of spatial detecting RNA molecules in a FFPE tissue sample comprises the steps of:
a1) deparaffinizing the FFPE tissue sample;
a2) acquiring an image of the tissue sample;
a3) identifying at least one ROI within the sample;
a4) applying a mask to the ROI including different predefined locations;
b) applying at least one species of oligonucleotide probes onto the predefined locations within the ROI and allowing the oligonucleotide probes to bind to the RNA molecules of the sample, wherein the oligonucleotide probes comprise a barcode sequence;
c) extracting the RNA-oligonucleotide probe complexes;
d) sequencing the extracted RNA molecules;
e) correlating the sequenced RNA molecules to the initial location of the corresponding target RNA molecule within the ROI to generate a spatial distribution of the targeted RNA molecules; wherein each location is identified by one or more species of oligonucleotides bound in step b).

In a specific embodiment the method of spatial detecting RNA in a FFPE tissue sample comprises the steps of:
a1) deparaffinizing the FFPE tissue sample;
a2) acquiring an image of the tissue sample;
a3) identifying at least one ROI within the sample;
a4) applying a mask to the ROI including different predefined locations;
b) applying 5'-RNA probes and 3'-RNA probes onto the predefined locations within the ROI and allowing the RNA probes to ligate to the 5'-end and the 3'-end of the RNA molecules of the sample, wherein the RNA probes comprise a barcode sequence;
c) extracting the RNA-RNA probe complexes;
d) sequencing the extracted RNA molecules;
e) correlating the sequenced RNA molecules to the initial location of the corresponding target RNA molecule within the ROI to generate a spatial distribution of the targeted RNA molecules; wherein each location is identified by one or more species of RNA probes bound in step b).

In a specific embodiment the method of spatial detecting RNA in a FFPE tissue sample comprises the steps of:
a1) deparaffinizing the FFPE tissue sample;
a2) acquiring an image of the tissue sample;
a3) identifying at least one ROI within the sample;
a4) applying a mask to the ROI including different predefined locations;
b) applying 5'-RNA probes and 3'-RNA probes onto the predefined locations within the ROI and allowing the RNA probes to ligate to the 5'-end and the 3'-end of the RNA molecules of the sample, wherein the RNA probes comprise a barcode sequence, and simultaneously applying a DNA molecule introducing a restriction site on the ligation site of the RNA probes dimer and a restriction enzyme that is suitable to cleave the restriction site;
c) extracting the RNA-RNA probe complexes;
d) sequencing the extracted RNA molecules;
e) correlating the sequenced RNA molecules to the initial location of the corresponding target RNA molecule within the ROI to generate a spatial distribution of the targeted RNA molecules; wherein each location is identified by one or more species of RNA probes bound in step b).

In a specific embodiment the method of spatial detecting RNA in a FFPE tissue sample comprises the steps of:
a1) deparaffinizing the FFPE tissue sample;
a2) acquiring an image of the tissue sample;
a3) identifying at least one ROI within the sample;
a4) applying a mask to the ROI including different predefined locations;
b) applying 5'-RNA probes and 3'-RNA probes onto the predefined locations within the ROI and allowing the RNA probes to ligate to the 5'-end and the 3'-end of the RNA molecules of the sample, wherein the RNA probes comprise a barcode sequence, and simultaneously applying a DNA molecule introducing a HaeIII restriction site on the ligation site of the RNA probes dimer and a HaeII restriction enzyme
c) extracting the RNA-RNA probe complexes;
d) sequencing the extracted RNA molecules;
e) correlating the sequenced RNA molecules to the initial location of the corresponding target RNA molecule within the ROI to generate a spatial distribution of the targeted RNA molecules; wherein each location is identified by one or more species of RNA probes bound in step b).

In a specific embodiment the method of spatial detecting DNA in a tissue sample comprises the steps of:
a1) acquiring an image of the tissue sample;
a2) identifying at least one ROI within the sample;
a3) applying a mask to the ROI including different predefined locations;
b) applying at least one species of oligonucleotide probes onto the predefined locations within the ROI and allowing the oligonucleotide probes to bind to the DNA molecules of the sample, wherein the oligonucleotide probes comprise a barcode sequence;
c) extracting the DNA-oligonucleotide probe complexes;
d) sequencing the extracted DNA molecules;
e) correlating the sequenced DNA molecules to the initial location of the corresponding target DNA molecule within the ROI to generate a spatial distribution of the targeted DNA molecules; wherein each location is identified by one or more species of oligonucleotide probes bound in step b).

Examples

Protocol types for the binding of the oligonucleotide probe to the nucleic acid molecule

|  | RNA | DNA |
|---|---|---|
| Hybridization | [A] Target probe/oligo dT, PCR | [B] Fragmentation, denaturation, hybridization, PCR |
| Ligation Blunt Sticky | [C] End specific ligation | [D] Fragmentation, ligation [E] Digestion, ligation |

Method for Spatial Detecting RNA in a FFPE Tissue Sample (Example According to Protocol Type [C])

Material: FFPE tissue sample on a slide

The tissue sample is treated with Proteinase K (ProtK) at 37° C., e.g. as described by Tullis and Rubin (Analytical Biochemistry, 1980, 107(1): 260-264) or using Proteinase K from *Engyodontium album* (Sigma-Aldrich) according to the manufacturer's instructions, followed by heat deactivation of ProtK for 15 minutes at 80° C.

The tissue sample is deparaffinized, e.g. using deparaffinization solution (e.g. Qiagen) according to the manufacturer's instructions.

An image of the complete slide is acquired (Philips Digital Pathology Scanner UFS) and within the image a ROI is identified.

Within the ROI different locations are selected and a top selection mask is applied by inkjet printing (print head XAAR) a UV curable ink (Sunjet ink Crystal UFE 7573 (Black)) creating a lattice that separates the different reaction wells. UV curing of the mask is carried out at 360 to 380 nm with a UV-LED for 30 s to 60 s.

A unique combination of two species of oligonucleotide probes comprising the barcode sequences (5'-RNA probes and 3'-RNA probes) is applied onto each predefined location by inkjet printing (using a FUJIFILM Dimatix printhead). The 5'-RNA probes and 3'-RNA probes are ligated to the mRNA molecules in a single step using a modified protocol of the NEBNext® Small RNA library prep set for Illumina® (NEB). In the standard protocol depicted in FIG. 2B) the RNA probes are ligated to the RNA molecule in a single step. During this reaction the 5'-RNA probes react with the 3'-RNA probes and form dimers. In the modified protocol instead of using a RT-primer for quenching the reaction a different approach is taken: In order to cleave these dimers a DNA molecule complementary to the ligation site of the 3'-end of the 5'-RNA probe and the 5'-end of the 3'-RNA probe is used that introduces a HaeIII restriction site on the ligation site of the RNA probe dimer. The DNA molecule is modified on both ends so that it does not participate in the ligation reaction. By the addition of the HaeIII restriction enzyme, RNA probe dimers with the complementary RNA-DNA hetroduplex will be cleaved on the ligation site of the two RNA probes only on the RNA strand while the DNA molecule stays intact. The cleaved RNA probes can participate again in the ligation reaction.

After the application of the ligation mix the slide is covered with a lid (Grace Bio-Labs HybriWell™ sealing system, SecureSeal™ adhesive chamber).

After ligation of the oligonucleotide probes, extraction buffer is applied to the sample immersing all wells and RNA extraction is performed using RNA membrane purification, e.g. using the RNeasy FFPE Kit (Qiagen) according to the manufacturer's instruction. The sample is heated during extraction and remains sealed in order to avoid dehydration of the sample. Alternatively, the sequence of the oligonucleotide probe can be used during the purification process, e.g. using magnetic beads. An incubation with DNase is carried out during or after the ligation RNA purification (e.g. at 37° C. for 15 min) followed by DNase inactivation at 80° C. for 15 min. Alternatively, DNase treatment may be conducted in parallel to the Proteinase K treatment step described above.

The RNA sequencing library preparation is performed using, e.g. the ScriptSeq v2 RNA-Seq Library Preparation Kit (Illumina) according to the manufacturer's instructions. RNA sequencing is performed and the barcoded transcripts are identified from the sequences. This information is then combined with the original image obtained from the ROI to build the spatial-transcriptional map.

Method for Spatial Detecting DNA in a FFPE Tissue Sample (Example According to Protocol Type [B])

Material: FFPE tissue sample on a slide

The tissue sample is deparaffinized, e.g. using deparaffinization solution (e.g. Qiagen) according to the manufacturer's instructions and dried.

The tissue sample is treated with Proteinase K (ProtK) at 37° C., e.g. as described by Tullis and Rubin (Analytical Biochemistry, 1980, 107(1): 260-264) or using Proteinase K from *Engyodontium album* (Sigma-Aldrich) according to the manufacturer's instructions, followed by heat deactivation of ProtK for 15 minutes at 80° C.

The tissue sample is washed with EtOH and dried 40° C. for 30 minutes. An image of the complete slide is acquired (Philips Digital Pathology Scanner UFS) and within the image a ROI is identified.

The DNA molecules are denaturated by addition of denaturation solution (70% formamide in 2×SSC, pH 7.0-8.0) and incubation at 75° C. for 5 minutes followed by incubation for 1 minute in 70% EtOH, 1 minute in 85% EtOH and 1 minute in 100% EtOH. Then slide is dried and placed at 45-50° C. to allow remaining EtOH to evaporate. Within the ROI different locations are selected and a top selection mask is applied by inkjet printing (print head XAAR) a UV curable ink (Sunjet ink Crystal UFE 7573 (Black)) creating a lattice that separates the different reaction wells. UV curing of the mask is carried out at 360 to 380 nm with a UV-LED for 30 s to 60 s.

Oligonucleotide probes comprising the barcode sequence are applied onto each predefined location by inkjet printing (using a FUJIFILM Dimatix printhead).

The tissue sample is incubated at 400 for 2 h (wet conditions).

After the incubation an elongation reaction is performed to amplify the target sequences which were hybridized using the primer sequence of the oligonucleotide probes.

After the elongation reaction the slide is covered with a lid (Grace Bio-Labs HybriWell™ sealing system, SecureSeal™ adhesive chamber).

The extraction buffer is introduced and the sample is incubated at 60° C. for 30 min.

DNA sequencing library preparation and DNA sequencing is performed and the barcoded transcripts are identified from the sequences. This information is then combined with the original image obtained from the ROI to build the spatial-transcriptional map. For the reactions of the above mentioned steps well-known standard kits are applied according to the manufacturer's protocol.

Method for One-Step 3' and 5' RNA Ligation with Two Different Barcodes on FFPE Slide The goal of this experiment was to ligate the miRNA cloning linker on the 3' side of RNA and to ligate the RNA 5'adapter on the 5' side of RNA on a FFPET slide in a single reaction. This was done according to the protocol described below. RT-qPCR assays were done on the extracted RNA to determine if ligation reaction was successful.

As sample we used 5 μM coupes, which were cut from a breast cancer FFPE block and baked for 30 minutes at 55-60° C. The slides were then transferred to an oven to ensure that samples were completely dry (overnight at 55° C.). The RNA has to become available/exposed on the slide for the ligation reaction to be successful. This was done by firstly, washing the slide in Xylyene (2×10 minutes 1×8 minutes), rinsing it with 100% EtOH (1×5 minutes, 1×1 minute). The slide was then air dried for 5 minutes and a hydrophobic barrier pen was used for creating a circle around the tissue in which fluids would stay (slide was air dried for another 15-30 minutes). A slide holder was filled with 1× pretreatment solution (Quantigene® View RNA Assay kit Affimetrix; P/N: 17428). The slide holder was placed in a waterbath (95° C.), and the slide was carefully placed in this slide holder with the heated 1× pretreatment solution for 20 minutes. Slide was rinsed in MiliQ water (2×1 minute) and PBS (1×5 seconds). An 200-400 μL aliquot of Protease QS solution (Quantigene® View RNA Assay kit Affimetrix; P/N: 16742) was added on the tissue and incubated for 20 minutes at 40° C. in a humidity box. The slide was washed in PBS (2×5 seconds) to remove Protease QS solution. Slide was then fixated in 4% buffered formaldehyde for 5 minutes at room temperature and excessive solution was again removed by washing the slide in PBS (2×5 seconds). We used two commercially available ligation kits: i) T4 RNA Ligase 2, truncated (New England BioLabs—M0242S) and ii) T4 RNA Ligase 1, ssRNA Ligase (New England BioLabs—M0204S). In addition a commercially available miRNA cloning linker (New England BioLabs—S1315S, SEQ ID=1) was used for the 3' ligation and a RNA oligo produced by IDT (SEQ ID=2) was used for the 5' ligation. A reaction mixture was prepared as described in the table below:

| Solution | Volume (μL) |
| --- | --- |
| 10x T4 RNA ligase reaction buffer | 6 |
| 50% PEG 8000 | 12 |
| 100 μM Universal miRNA cloning linker | 1.2 |
| 10 mM ATP | 6 |
| 100 μM RNA oligo | 3 |
| DMSO | 6 |
| T4 RNA Ligase 2, truncated (T4 Rnl2tr) | 3 |
| T4 RNA Ligase 1 | 6 |
| ddH2O | 16.8 |

A 60 μL aliquot of ligation solution was added to the tissue on the slide and incubated in a humidity box (1 hour at 25° C., and 1 hour at 37° C.). The ligation solution was stopped by washing the slide in PBS (2×5 seconds). RNA was collected by addition of 4 times 200 μL commercially available lysis buffer (Siemens Versant RNA isolation kit), on the tissue and transferring it to PCR clean 1.5 mL centrifuge tube. RNA was further isolated according to the manufacturers protocol (Siemens Versant RNA isolation kit).

Detection of ligated product was then determined with RT-qPCR assays specifically designed for the ligated product. See the amplification curves in FIG. 3 and the used oligonucleotides in the table below. The RT-qPCR assays detect ligated product on B-actin mRNA. We used a negative control, which was a slide treated the same as describe above but without the actual addition of the ligation sequences (cloning linker and RNA oligo), shown in red. We used a no template control (NTC) for the PCR control, shown in black. We used 1 RT-qPCR assay for determining the 3' ligation product, 1 RT-qPCR assay for determining the presence of the 5' ligation product and the final RT-qPCR assay as a control to determine total B-actin mRNA levels.

| FIG. | Oligo | Function | SEQ ID |
| --- | --- | --- | --- |
| 3A | F1 | Forward primer | 3 |
| 3A | R1 | Reverse primer | 4 |
| 3A | P1 | Taqman probe | 5 |
| 3B | F4 | Forward primer | 6 |
| 3B | R2 | Reverse primer | 7 |
| 3B | P1 | Taqman probe | 8 |
| 3C | F1 | Forward primer | 9 |
| 3C | R1 | Reverse primer | 10 |
| 3C | FAM | Taqman probe | 11 |

The invention claimed is:

1. A method for spatial detecting nucleic acids in a tissue sample comprising the steps of:
 separating the sample into at least a first layer and a second layer;
 applying at least one imaging label to the first layer;
 imaging the first layer;
 identifying at least one region of interest (ROI) within the sample from the image of the first layer and applying the ROI to the second layer;
 applying at least one species of oligonucleotide probes onto predefined locations within the ROI, said predefined locations defined by a full separation mask, wherein the full separation mask includes a lattice separation mask, and allowing the oligonucleotide probes to bind to the nucleic acids of the sample, wherein the oligonucleotide probes comprise a barcode sequence;
 extracting the nucleic acid-oligonucleotide probes complexes;
 sequencing the extracted nucleic acid molecules;
 correlating the sequenced nucleic acid molecules to the initial location of the corresponding targeted nucleic acid molecules within the ROI to generate a spatial distribution of the targeted nucleic acid molecules, wherein each location is identified by one or more species of oligonucleotide probes bound in the step of applying at least one species of oligonucleotide probes.

2. The method according to claim 1, wherein prior to the step of sequencing the extracted nucleic acid molecules, DNA molecules are generated from the nucleic acid-oligonucleotide probes complexes via DNA amplification.

3. The method according to claim 2, wherein the generation of DNA molecules occurs after a reverse transcription reaction.

4. The method according to claim 2, wherein in the step of applying at least one species of oligonucleotide probes, the binding of the oligonucleotide probes to the nucleic acids of the sample occurs via hybridization and wherein the oligonucleotide probes are used as primers.

5. The method according to claim 1, wherein in the step of applying at least one species of oligonucleotide probes, the binding of the oligonucleotide probes to the nucleic acids of the sample occurs via ligation.

6. The method according to claim 5, wherein the step of correlating the sequenced nucleic acid molecules further comprises correlating the spatial distribution of the targeted nucleic acid molecules with an image of the ROI or with an image of the tissue sample in which the ROI was identified obtained before or after the step of applying at least one species of oligonucleotide probes.

7. The method according to claim 6, wherein the method further comprises providing a two-dimensional spatial map to visualize the spatial distribution of the targeted nucleic acid molecules.

8. The method according to claim 7, wherein the method further comprises overlaying the two-dimensional spatial map with the image of the ROI or with the image of the tissue sample in which the ROI was identified obtained before or after the step of applying at least one species of oligonucleotide probes.

9. The method according to claim 1, wherein at least two different species of oligonucleotide probes are bound to one targeted nucleic acid molecule in the step of applying at least one species of oligonucleotide probes, and wherein the unique combination of the at least two different species of oligonucleotide probes is used to identify the location of the targeted nucleic acid molecules within the ROI.

10. The method according to claim 1, wherein at least one of the species of oligonucleotide probes that bind to one nucleic acid molecule comprises a generic sequence, wherein optionally the generic sequence is complementary to the targeted nucleic acid.

11. The method according to claim 10, wherein at least one of the species of oligonucleotide probes that bind to one nucleic acid molecule comprises an additional sequence, wherein the additional sequence is a purification sequence or a primer alignment sequence.

12. The method according to claim 1, wherein in the step of applying at least one species of oligonucleotide probes, the oligonucleotide probes are applied onto the predefined locations by liquid transfer technologies, preferably by contact printing techniques or non-contact printing techniques, such that the applied oligonucleotide probes do not intermix between different predefined locations.

13. The method according to claim 1, wherein the sample is a histopathological specimen, preferably a deparaffinised formalin-fixed paraffin-embedded (FFPE) sample, a fresh frozen (FF) sample or a fresh sample, or a cytology sample.

14. The method of claim 1, wherein the at least one imaging label applied to the first layer does not interfere with any of the steps of applying at least one species of oligonucleotide probes, extracting the nucleic acid-oligonucleotide probes complexes, or sequencing the extracted nucleic acid molecules performed on the second layer.

15. A method for spatial detecting nucleic acids in a tissue sample comprising the steps of:
separating the sample into at least a first layer and a second layer;
applying at least one imaging label to the first layer;
imaging the first layer;
identifying at least one region of interest (ROI) within the sample from the image of the first layer and applying the ROI to the second layer;
applying at least one species of oligonucleotide probes onto predefined locations within the ROI, said predefined locations defined by a freeform separation mask having an irregular shape based on the shape of the ROI, and allowing the oligonucleotide probes to bind to the nucleic acids of the sample, wherein the oligonucleotide probes comprise a barcode sequence;
extracting the nucleic acid-oligonucleotide probes complexes;
sequencing the extracted nucleic acid molecules;
correlating the sequenced nucleic acid molecules to the initial location of the corresponding targeted nucleic acid molecules within the ROI to generate a spatial distribution of the targeted nucleic acid molecules, wherein each location is identified by one or more species of oligonucleotide probes bound in the step of applying at least one species of oligonucleotide probes.

16. The method according to claim 15, wherein prior to the step of sequencing the extracted nucleic acid molecules, DNA molecules are generated from the nucleic acid-oligonucleotide probes complexes via DNA amplification.

17. The method according to claim 16, wherein the generation of DNA molecules occurs after a reverse transcription reaction.

18. The method according to claim 16, wherein in the step of applying at least one species of oligonucleotide probes, the binding of the oligonucleotide probes to the nucleic acids of the sample occurs via hybridization and wherein the oligonucleotide probes are used as primers.

19. The method according to claim 15, wherein in the step of applying at least one species of oligonucleotide probes, the binding of the oligonucleotide probes to the nucleic acids of the sample occurs via ligation.

20. The method according to claim 19, wherein the step of correlating the sequenced nucleic acid molecules further comprises correlating the spatial distribution of the targeted nucleic acid molecules with an image of the ROI or with an image of the tissue sample in which the ROI was identified obtained before or after the step of applying at least one species of oligonucleotide probes.

21. The method according to claim 20, wherein the method further comprises providing a two-dimensional spatial map to visualize the spatial distribution of the targeted nucleic acid molecules.

22. The method according to claim 21, wherein the method further comprises overlaying the two-dimensional spatial map with the image of the ROI or with the image of the tissue sample in which the ROI was identified obtained before or after the step of applying at least one species of oligonucleotide probes.

23. The method according to claim 15, wherein at least two different species of oligonucleotide probes are bound to one targeted nucleic acid molecule in the step of applying at least one species of oligonucleotide probes, and wherein the unique combination of the at least two different species of oligonucleotide probes is used to identify the location of the targeted nucleic acid molecules within the ROI.

24. The method according to claim 15, wherein at least one of the species of oligonucleotide probes that bind to one nucleic acid molecule comprises a generic sequence, wherein optionally the generic sequence is complementary to the targeted nucleic acid.

25. The method according to claim 24, wherein at least one of the species of oligonucleotide probes that bind to one nucleic acid molecule comprises an additional sequence, wherein the additional sequence is a purification sequence or a primer alignment sequence.

26. The method according to claim 15, wherein in the step of applying at least one species of oligonucleotide probes, the oligonucleotide probes are applied onto the predefined locations by liquid transfer technologies, preferably by contact printing techniques or non-contact printing techniques, such that the applied oligonucleotide probes do not intermix between different predefined locations.

27. The method according to claim 15, wherein the sample is a histopathological specimen, preferably a deparaffinised formalin-fixed paraffin-embedded (FFPE) sample, a fresh frozen (FF) sample or a fresh sample, or a cytology sample.

28. The method of claim 15, wherein the at least one imaging label applied to the first layer does not interfere with any of the steps of applying at least one species of oligonucleotide probes, extracting the nucleic acid-oligonucleotide probes complexes, or sequencing the extracted nucleic acid molecules performed on the second layer.

* * * * *

SEQUENCE LISTING

<160> NUMBER OF SEQ ID NOS: 11

<210> SEQ ID NO 1
<211> LENGTH: 16
<212> TYPE: DNA
<213> ORGANISM: Artificial Sequence
<220> FEATURE:
<223> OTHER INFORMATION: Universal miRNA Cloning Linker (New England
      BioLabs - S1315S), n in position 1 = t modified at the 5' end with
      rApp, n in position 16 = t modified at the 3' end with -NH2

-continued

<220> FEATURE:
<221> NAME/KEY: misc_feature
<223> OTHER INFORMATION: n in position 1 = t modified at the 5' end with
rApp, n in position 16 = t modified at the 3' end with -NH2

<400> SEQUENCE: 1
ngtaggcacc atcaan 16

<210> SEQ ID NO 2
<211> LENGTH: 52
<212> TYPE: RNA
<213> ORGANISM: Artificial Sequence
<220> FEATURE:
<223> OTHER INFORMATION: RNA oligo

<400> SEQUENCE: 2
rgrururcra rgrargruru rcrurarcra rgrurcrcrg rarcrgraru rc 52

<210> SEQ ID NO 3
<211> LENGTH: 17
<212> TYPE: DNA
<213> ORGANISM: Artificial Sequence
<220> FEATURE:
<223> OTHER INFORMATION: forward primer for 3' ligation validation

<400> SEQUENCE: 3
gaggcagcca gggctta 17

<210> SEQ ID NO 4
<211> LENGTH: 23
<212> TYPE: DNA
<213> ORGANISM: Artificial Sequence
<220> FEATURE:
<223> OTHER INFORMATION: reverse primer for 3' ligation validation

<400> SEQUENCE: 4
attgatggtg cctacagtca ttt 23

<210> SEQ ID NO 5
<211> LENGTH: 27
<212> TYPE: DNA
<213> ORGANISM: Artificial Sequence
<220> FEATURE:
<223> OTHER INFORMATION: Taqman probe for 3' ligation validation, ZEN
(quencher) located between positions 9 and 10
<220> FEATURE:
<221> NAME/KEY: misc_feature
<223> OTHER INFORMATION: n in position 9 = c modified at the 3' end with
ZEN (quencher)

<400> SEQUENCE: 5
cctgtacant gacttgagac cagttga 27

<210> SEQ ID NO 6
<211> LENGTH: 17
<212> TYPE: DNA
<213> ORGANISM: Artificial Sequence
<220> FEATURE:
<223> OTHER INFORMATION: forward primer for 5' ligation validation

<400> SEQUENCE: 6
acagtccgac gatcacc 17

<210> SEQ ID NO 7
<211> LENGTH: 18
<212> TYPE: DNA
<213> ORGANISM: Artificial Sequence

```
<220> FEATURE:
<223> OTHER INFORMATION: reverse primer for 5' ligation validation

<400> SEQUENCE: 7
agcgcggcga tatcatca                                                   18

<210> SEQ ID NO 8
<211> LENGTH: 22
<212> TYPE: DNA
<213> ORGANISM: Artificial Sequence
<220> FEATURE:
<223> OTHER INFORMATION: Taqman probe for 5' ligation validation, ZEN
      (quencher) located between positions 9 and 10
<220> FEATURE:
<221> NAME/KEY: misc_feature
<223> OTHER INFORMATION: n in position 9 = t modified at the 3' end with
      ZEN (quencher)

<400> SEQUENCE: 8
acagagccnc gcctttgccg at                                              22

<210> SEQ ID NO 9
<211> LENGTH: 18
<212> TYPE: DNA
<213> ORGANISM: Artificial Sequence
<220> FEATURE:
<223> OTHER INFORMATION: forward primer for total beta-actin
      determination

<400> SEQUENCE: 9
ccaaccgcga gaagatga                                                   18

<210> SEQ ID NO 10
<211> LENGTH: 20
<212> TYPE: DNA
<213> ORGANISM: Artificial Sequence
<220> FEATURE:
<223> OTHER INFORMATION: reverse primer for total beta-actin
      determination

<400> SEQUENCE: 10
ccagaggcgt acagggatag                                                 20

<210> SEQ ID NO 11
<211> LENGTH: 23
<212> TYPE: DNA
<213> ORGANISM: Artificial Sequence
<220> FEATURE:
<223> OTHER INFORMATION: Taqman probe for total beta-actin determination

<400> SEQUENCE: 11
ccatgtacgt tgctatccag gct                                             23
```